US005654398A

United States Patent [19]
Frankel et al.

[11] Patent Number: 5,654,398
[45] Date of Patent: Aug. 5, 1997

[54] COMPOSITIONS AND METHODS FOR INHIBITING REPLICATION OF HUMAN IMMUNODEFICIENCY VIRUS-1

[75] Inventors: Alan Frankel, Tiburon; Ruoying Tan, San Francisco; Derek Hudson, San Anselmo, all of Calif.

[73] Assignee: The Regents of the University of California, Oakland, Calif.

[21] Appl. No.: 71,811

[22] Filed: Jun. 3, 1993

[51] Int. Cl.$^6$ ..................................................... C07K 7/06
[52] U.S. Cl. ........................................... 530/327; 530/328
[58] Field of Search ..................................... 530/323, 326, 530/327, 328, 329, 332; 435/5, 6

[56] References Cited

FOREIGN PATENT DOCUMENTS

| | | |
|---|---|---|
| WO91/10453 | 7/1991 | WIPO . |
| WO92/05195 | 4/1992 | WIPO . |
| WO92/06212 | 4/1992 | WIPO . |
| WO92/07871 | 5/1992 | WIPO . |

OTHER PUBLICATIONS

Bartel et al. (1991), Cell, 67:529–536.
Tiley et al. (1992), Proc. Natl. Acad. Sci. USA, 89:758–762.
Chin (1992), Journal of Virology, pp. 600–607.
Heaphy et al. (1991), Proc. Natl. Acad. Sci. USA, 88:7366–7370.
Kjems et al. (1991), Cell, 67:169–178.
Kjems et al. (1992), EMBO Journal, 3:1119–1129.

Primary Examiner—David Guzo
Attorney, Agent, or Firm—Townsend and Townsend and Crew LLP

[57] ABSTRACT

Compositions and methods for identifying compositions which inhibit binding of the Rev protein to the Rev-responsive element in cells infected by HIV-1 are provided. The compositions display or mimic the electronic configuration of a binding domain within the native Rev protein, but are free from those portions responsible for REV activity and are preferably modified to display enhanced binding affinity to the RRE. Screening methods for identifying polypeptides and other compositions having such enhanced binding affinity are also described.

6 Claims, 11 Drawing Sheets

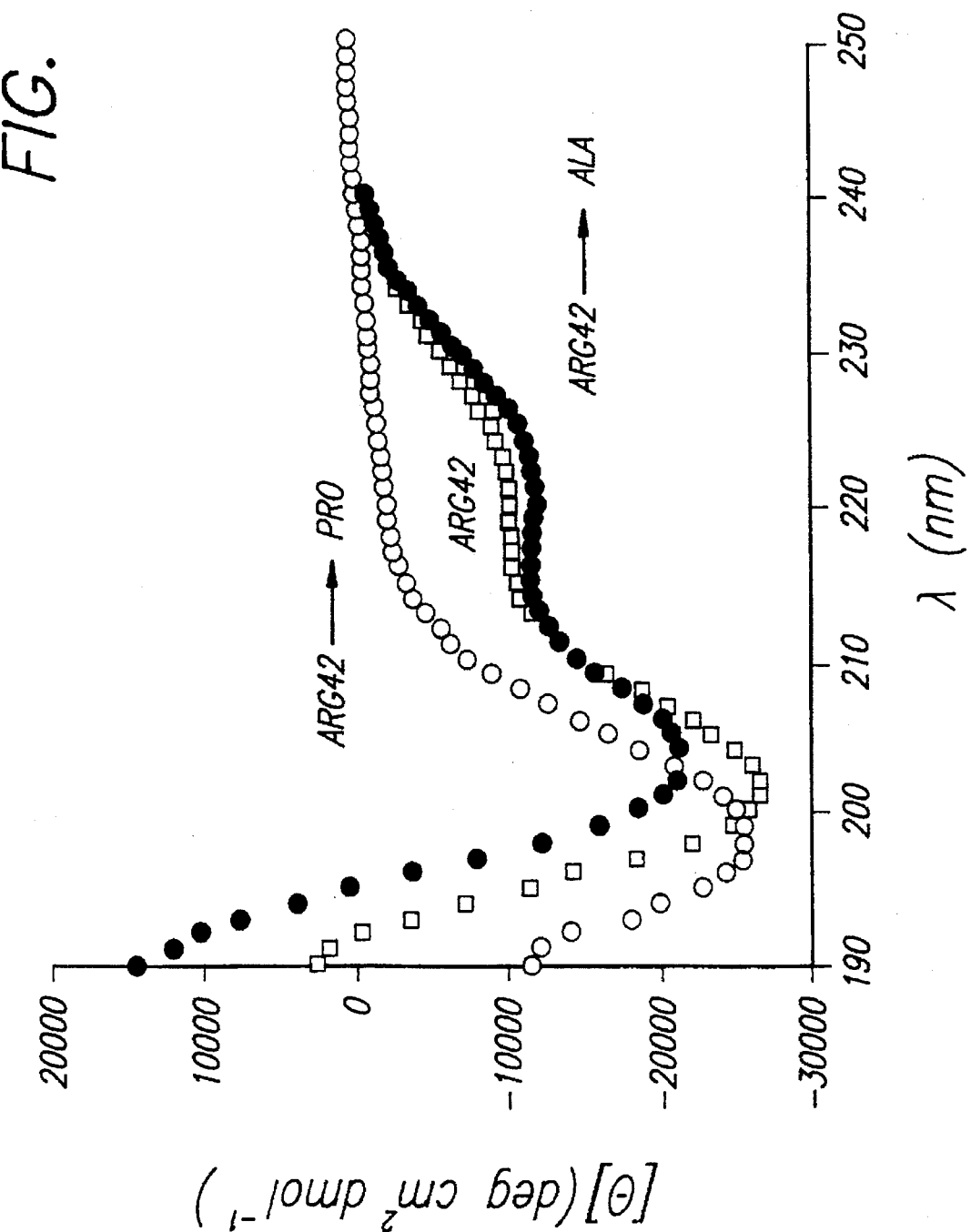

(I)     Tat 1-48     TRQARRNRRRRWRERQR (II)     AAAATRQARRNRRRRWRERQR (III)     TRQARRNRRRRWRERQRAAAAR (IV)     AAAATRQARRNRRRRWRERQRAAAAR (Tat)     RKKRRQRRRP

Rev-RRE

COMPOSITIONS AND METHODS FOR INHIBITING REPLICATION OF HUMAN IMMUNODEFICIENCY VIRUS-1

This invention was made with Government support under Grant No. 7 R01 AI 29135-04, awarded by the National Institutes of Health. The Government has certain rights in this invention.

BACKGROUND OF THE INVENTION

1. Field of the Invention

The present invention relates generally to compositions and methods for inhibiting replication of human immunodeficiency virus (HIV)-1. More particularly, the present invention provides polypeptide compositions which interfere with binding between the Rev protein and Rev-responsive element (RRE) of HIV-1, which binding is essential for HIV-1 replication.

The Rev protein of HIV-1 is a gene regulatory protein that is essential for viral replication. Although the exact function of Rev is not understood, it is known that it is essential to facilitate transport of unspliced viral mRNA from the cell nucleus to the cytoplasm. The unspliced mRNA is then translated into viral structural proteins which are assembled into infectious viral particles. The Rev protein must bind to a site within the mRNA, referred to as the IIB site of the Rev-responsive element (RRE), which is a stem-loop structure containing an asymmetric internal budge and at least one non-Watson-Crick base pair. It has been previously shown that a synthetic peptide including amino acids 34–50 of the Rev protein is sufficient for specific binding to the IIB site.

As binding between the Rev protein and the RRE is essential for HIV-1 replication, it would be desirable to identify and provide compositions capable of blocking or interfering with such binding in order to prevent or inhibit such replication. In particular, it would be desirable to provide compositions which are able to specifically bind to the IIB site of the RRE but which will not provide the essential Rev protein function. Desirably, such compounds will bind to the RRE in preference to native Rev protein, displaying a greater affinity and/or specificity for the IIB binding site than the native protein. Such compositions should be stable and suitable for incorporation into pharmaceutical products for administration to humans. It would be further desirable to provide in vitro and in vivo methods for screening test compounds to identify those compounds which are able to effectively compete with native Rev protein for binding to the RRE, which test compounds would be suitable for further screening for effectiveness as therapeutic agents for the treatment of HIV-1 infection.

2. Description of the Background Art

Binding between the Rev gene product and the Rev-responsive element (RRE) in HIV is described in Heaphy et al. (1991) Proc. Natl. Acad. Sci. USA 88:7366–7370; Bartel et al. (1992) Proc. Natl. Acad. Sci. USA 89:758–762. Binding between a 17 amino acid peptide corresponding to residues 34–50 of Rev was shown in Kjems et al. (1991) Cell 67:169–178 and (1992) EMBO J. 11:1119–1129. Inhibition of binding between Rev and RRE as a therapy for HIV-1 infection is proposed in, e.g., Rosen (1992) J. Virol. 66:600–607. Therapeutic strategies for HIV-1 infection are proposed in the following published PCT patent applications: W092/07871; W092/05195; and W091/10453. The expression of the Rev protein of HIV-1 in Drosophila cells is described in W092/06212.

SUMMARY OF THE INVENTION

The present invention provides compositions and methods for identifying compositions which inhibit binding between the Rev protein and the Rev-responsive element of HIV-1. The compositions include a molecule or compound having a molecular weight below 5 kD and a stabilized molecular configuration which presents key functional groups, identified herein, so that high affinity/specificity binding is achieved to the IIB site on RRE. The affinity should be at least equal to and preferably greater than that of the native Rev protein. In this way, administration of the compositions of the present invention to cells can inhibit replication of HIV-1 by interfering with or blocking essential binding of the endogenous Rev protein to the RRE.

Compositions according to the present invention may be peptidic or non-peptidic, with exemplary compositions being polypeptides having 30 or fewer amino acid residues with a stabilized α-helical conformation. The polypeptides will preferably include at least six non-contiguous amino acids from the wild-type Rev protein, which amino acids have been found to be essential for binding between the Rev protein and the RRE. The remaining amino acids may be the same as or different from the corresponding amino acids in the native Rev protein, preferably including at least some modifications (i.e., substitutions, additions and/or deletions) which enhance binding affinity and/or α-helical stabilization. Additionally, the N-terminus, the C-terminus, or both, may be modified or derivatized to enhance the RRE binding affinity and/or α-helical stabilization. Such compositions may be in the form of pharmaceutical compositions including a carrier or vehicle suitable for administration to humans.

The present invention still further provides screening methods for identifying compositions capable of inhibiting binding of the Rev protein to the RRE. Such screening methods rely on measuring the ability of test compounds, particularly compositions according to the present invention, to inhibit binding of native Rev protein to RRE in cell culture. Cultured cells which express a Rev-RRE-dependent reporter gene are modified to also express a potentially inhibitory test polypeptide. Expression of the reporter gene can then be related to binding inhibition of the Rev protein as a result of the in situ produced test polypeptide.

Pharmaceutical compositions according to the present invention will comprise compounds which inhibit binding of the Rev protein to the RRE present in a pharmaceutically acceptable carrier.

BRIEF DESCRIPTION OF THE DRAWINGS

FIG. 3 (parts A–C)

FIG. 4: (parts A–B) FIG. 4A presents circular dichroism spectra for wild-type (Arg 42 indicated by □) and mutant (Arg 42→Pro indicated by O and Arg → Ala indicated by ●) Rev peptides.

FIG. 5 (parts A–C)

FIG. 6 (parts A–B)

DESCRIPTION OF SPECIFIC EMBODIMENTS

According to the present invention, compositions are provided which compete with the endogenous Rev protein for binding to the IIB site in the Rev-responsive element (RRE) in cells infected with HIV-1. The compositions may be peptidic or non-peptidic and will possess a binding affinity which is at least equal to and preferably greater than that of the endogenous Rev protein to the RRE. Such relative binding affinities may be determined in vitro or in vivo, as described in greater detail hereinafter. The compositions will provide competitive binding inhibition of the Rev protein when introduced to cells infected with HIV-1 and are thus suitable as pharmaceutical compositions for the treatment of HIV-1 infection.

The compositions of the present invention include active molecules (compounds) which will be appropriately sized, or otherwise modified with chemical substituents, so that they may penetrate the cell membrane when administered to HIV-1 infected cells, particularly when administered to an infected patient for treatment of HIV-1 infection. The compositions will thus comprise active molecules (i.e., molecules which can compete with native Rev for binding to the RRE) having molecular weight below about 5 kD, usually below about 3 kD, and often below about 2 kD for polypeptides and below 1 kD for non-peptidic compounds. The polypeptide compositions will usually have 30 or fewer amino acids, preferably having 25 or fewer, more preferably having 15 or fewer, and frequently consisting essentially of an 11-mer including the essential binding amino acids, as described below.

Exemplary peptidic compositions will comprise polypeptide molecules which include an RRE binding domain but which lack other portions of the Rev protein which are responsible for HIV-1 replication activity. The Rev protein has a full length of 116 amino acids, and it has been found that amino acids 34–50 of the native protein (based on the numbering set forth in Kjems et al. (1992), supra.) define the binding domain and include six non-contiguous amino acid residues which are essential for binding to the RRE. The sequence of the binding domain of the Rev protein (SEQ ID NO:1) (with the essential binding amino acids being marked with *) is as follows:

Thr*—Arg*—Gln—Ala—Arg*—Arg*—Asn*—  SEQ ID NO: 1
34    35    36   37    38    39    40

Arg—Arg—Arg—Arg*—Trp—Arg—Glu—Arg—Gln—Arg
41   42   43   44    45   46   47   48   49  50

Figure 6A:
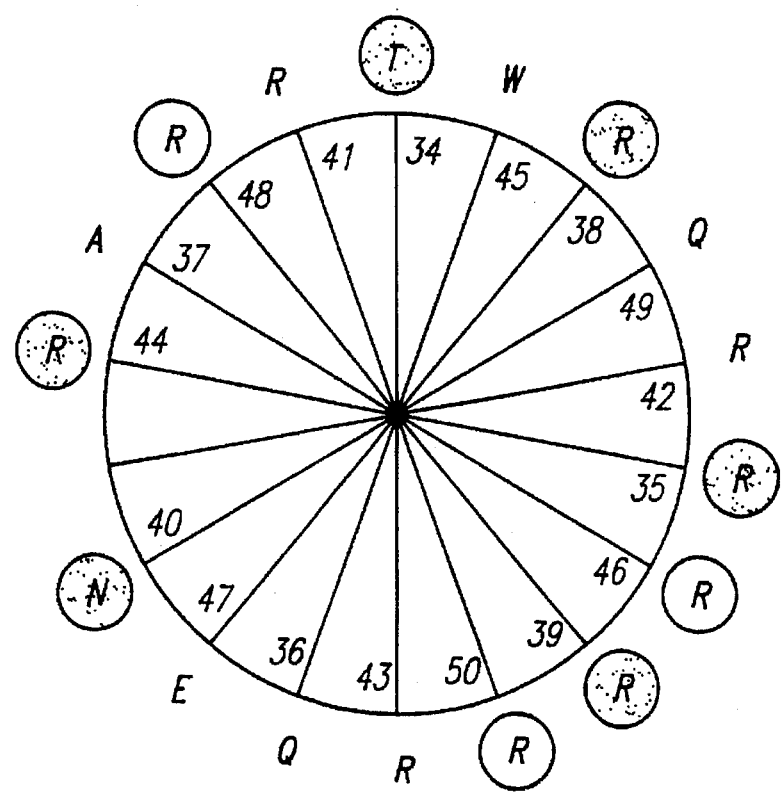
FIG. 6A is a helical projection of Rev$_{34-50}$ showing the essential amino acid binding peptides in shaded circles.
Figure 6B:
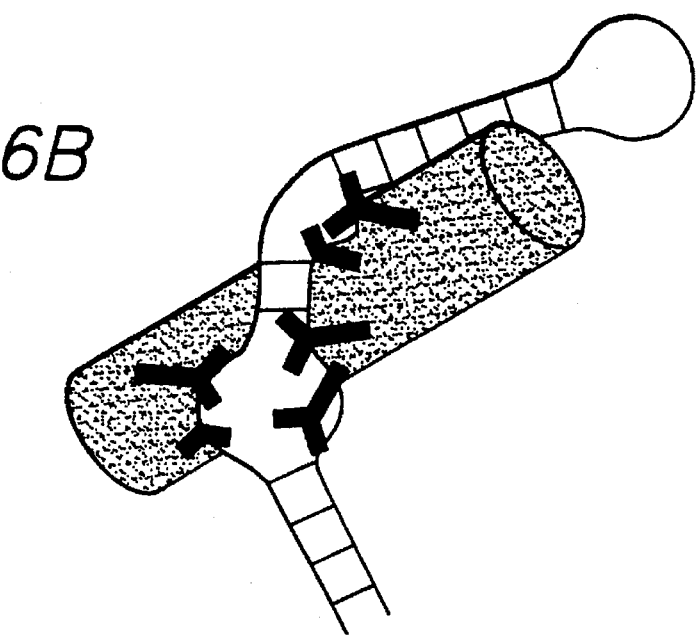
FIG. 6B is a schematic illustration of the binding of Rev (shaded cylinder) to the RRE with the side chains of the essential amino acids being shown in black.

FIG. 6A is a helical projection illustrating the peripheral distribution of the essential amino acids about the α-helical peptide backbone. FIG. 6B is a probable binding configuration of the Rev peptide to the RRE with the binding side chains of the essential amino acids shown in black line.

The active polypeptide molecules of the present invention will thus preferably include at least a portion of the following 11-mer sequence SEQ ID NO:11):

T—A$_1$—X$_1$—X$_2$—A$_2$—A$_3$—A$_4$—X$_3$—X$_4$-X$_5$—A$_4$ SEQ ID NO:2 wherein X$_{1-5}$ may be any natural or unnatural L-amino acid and may be the same or different from each other, preferably being lysine or alanine. A$_{1-4}$ will preferably be arginine, but may also be mimetic derivatives of arginine, such as homoarginine, citrulline, guanidophenylalanine, and other N-guanido methylated forms thereof. T is preferably threonine, but may also be serine and mimetic threonine derivatives, such as homothreonine, dehydrothreonine, and the like. As is preferably asparagine, but may also be glutamine, citrulline, and other amide functionalized amino acid residues. The polypeptides will include at least three contiguous residues from the above sequence, preferably including at least six contiguous residues, frequently including at least eight residues, and often including the entire 11-mer sequence.

It will frequently be desirable to substitute, delete or insert alternative amino acid residues at these non-essential positions designated X in the above sequence. In particular, it will be desirable to modify the polypeptide compositions of the present invention to enhance the α-helical conformation of the polypeptides. As described in detail in the Experimental Section hereinafter, the 17 amino acid residue polypeptide comprising the binding region of the native Rev protein possesses an α-helical conformation which is necessary for binding to the RRE. The polypeptides of the present invention will generally be modified to further enhance the α-helical content above that of the wild-type polypeptide. For example, the α-helix may be stabilized by substitution of the non-essential amino acids with other amino acids having high helical propensities, such as alanine, and the like. Additionally or alternatively, the non-essential amino acids may be substituted with amino acids which stabilize interactions between amino acid side chains and the RNA, such as lysine, and the like. Further stabilization may be provided by the incorporation of side chain-to-side chain covalent bonds (e.g., between lysine and aspartic acid or glutamic acid, and the like) in parts of the structure which are removed from direct interaction with the RNA. Additionally, the polypeptide termini may be modified by covalent attachment of functional groups to affect electrostatic interactions to stabilize the helix macrodipole. Finally, amino acids may be added an the N-terminus or C-terminus to cap the helix with additional hydrogen bonds, further affording stability. Thus, preferred active polypeptide molecules according to the present invention will include the above-identified 11-mer, more preferably consisting essentially of the 11-mer with modification as described, but being free from the remaining amino acids of the native Rev sequence. Such preferred modified active polypeptide molecules may then be tested for binding affinity, as described in more detail hereinbelow.

Optimal peptide sequences of the polypeptides of the present invention can be obtained by preparation of modified polypeptides and verification of RRE binding by such screening techniques. For example, peptides can be synthesized to contain the six non-contiguous essential amino acids at their fixed relative positions as set forth above, while the non-essential amino acids (X) are randomly selected, preferably with combinations of lysine and alanine. Lysines provide additional non-electrostatic contacts which tend to increase overall RNA-binding affinity, and alanine enhances helical content of the polypeptide, as described above. Specific screening methods are described below.

Polypeptides of the present invention may be produced by either of two general approaches. Frequently, and particularly for initial testing, polypeptides may be synthesized by the well-known Merrifield solid-phase chemical synthesis method where amino acids are sequentially added to a growing chain on a solid phase. See, Merrifield, J. Am. Chem. Soc. 85:2149–2156 (1963). Conveniently, the polypeptides of the present invention may be synthesized in automated equipment provided by commercial suppliers, such as Applied Biosystems, Inc. of Foster City, Calif. and Millipore Corporation, Beford, Mass. Alternatively, polypeptides can be manually synthesized by techniques which are well-described in the scientific and patent literature.

The polypeptides of the present invention may also be synthesized by recombinant techniques involving the expression in cultured cells of recombinant DNA molecules encoding the gene for a desired polypeptide sequence. The gene encoding the polypeptide sequence may itself be natural or synthetic. Conveniently, polynucleotides may be synthesized by well-known techniques. For example, short single-stranded DNA fragments may be prepared by phosphoramidite method first described by Beaucage and Carruthers. A double-stranded fragment may then be obtained, either by synthesizing the complementary strand and annealing the strands together under appropriate conditions, or by adding the complementary strand using DNA polymerase and an appropriate primer sequence. The natural or synthetic DNA fragments coding for the desired polypeptide sequence will be incorporated into suitable DNA constructs capable of introduction to and expression in an in vitro cell culture. Usually, the DNA constructs will be suitable for replication in a unicellular host, such as yeast or bacteria, and will preferably also be capable of introduction and integration within the genome of cultured mammalian or other eukaryotic cells lines. DNA constructs prepared for introduction into bacteria or yeast will include a replication system recognized by the host, the DNA fragment encoding the desired polypeptide sequence, transcriptional and translational initiation regulatory sequences joined to the 5'-end of the polypeptide coding sequence, and transcriptional and translational termination regulatory sequences joined to the 3'-end of the coding sequence. The transcriptional regulatory sequences will include a heterologous promoter that is recognized by the host. Conveniently, expression vectors that include the replication system and transcriptional and translational regulatory sequences, together with an insertion site for the polypeptide coding sequence, are commercially available and may be readily employed.

The active polypeptides of the present invention will be obtained in a substantially pure form, typically being at least 50% weight/weight (w/w) or higher purity, and being substantially free of interfering proteins and contaminants, such as those which may result from expression in cultured cells. Preferably, the peptides are purified to at least 80% w/w purity, more preferably to at least 95% w/w purity. For use in pharmaceutical compositions, as described hereinafter, the polypeptide purity should be very high, typically being at least 99% w/w purity, and preferably being higher. Such purity may be achieved by a variety of conventional separation techniques, such as reverse-phase high performance liquid chromatography.

Compositions of the present invention may also employ non-peptidic active molecules. The non-peptidic molecules should have a stabilized electronic configuration and molecular conformation that allows key functional groups to be presented to the RRE RNA in substantially the same way as they are in the native protein and/or in the $Rev_{34-50}$ peptide as illustrated in FIGS. 6A and 6B. The spatial position of the functional groups and moieties should be selected to mimic the side-chain groups of the essential amino acids of the Rev binding domain, thus being able to bind to the IIB site of the RRE with an affinity at least equal to, and preferably greater than, that of native Rev protein. In particular, the non-peptidic compounds will have spatial electronic properties which are comparable to the polypeptide binding region, but will typically be much smaller molecules than the polypeptides, frequently having a molecular weight below about 2 kD and preferably below about 1 kD.

Identification of such non-peptidic compounds can be performed through use of techniques known to those working in the area of drug design. Such techniques include, but are not limited to, self-consistent field (SCF) analysis, configuration interaction (CI) analysis, and normal mode dynamics analysis. Computer programs for implementing these techniques are readily available. See Rein et al. *Computer-Assisted Modeling of Receptor-Ligand Interactions,* Alan Liss, New York (1989).

Preparation of such identified compounds will depend on the desired characteristics of the compound and will frequently involve standard chemical synthesis techniques, such as are well-described in the patent and scientific literature. Non-peptidic active molecules and compounds will preferably be synthesized to display or mimic the six essential non-contiguous amino acids identified in the RRE binding domain of the Rev protein. Preferably, such molecules will have a backbone which permits a helical arrangement of the moieties which mimic the electronic characteristics of the side chains, so that binding to the RRE can be achieved. It may also be possible to design small molecules which inhibit binding of fewer than all of the six essential amino acid functional groups. As each of these six functionalities is essential for RNA binding by the native protein, a small molecule designed to inhibit only a few of the interactions (including only one binding interaction) should be effective to prevent RNA-Rev productive interaction.

Screening methods according to the present invention include both in vitro and in vivo techniques. In vitro techniques comprise methods where a test compound, usually a polypeptide or polypeptide mimetic molecule prepared as described above, will be exposed to the binding region of RRE in the presence of wild-type Rev protein or another polypeptide or compound which is known to bind to the RRE with an affinity equal to or greater than wild type. In this way, a competition is set up between the Rev protein and the test compound, whereby relative binding of the two competing species to the RRE is indicative of which compound has a higher binding affinity. This approach, of course, assumes that the compounds possess similar kinetic characteristics so that binding distribution is primarily a function of affinity. For example, either the Rev protein or an RRE polynucleotide can be immobilized on a solid phase, with the other component being exposed to the solid phase in presence of the test compound. Binding distribution can then be measured using label(s) attached to either mobile component in the system. Alternatively, gel shift assays may be used as described in detail in the Experiment Section hereinafter.

In vivo screening methods would employ cultured cells which include a reporter system for Rev activity. Such reporter systems are described in the literature. See, e.g., Zupp et al. (1991) Proc. Natl. Acad. Sci. USA 88:7734 and McDonald et al. (1992) J. Virol. 66:7232, the disclosures of which are incorporated herein by reference. Soluble polypeptides or other small molecules would be added directly to the cell culture, with the effect on Rev function being observed. The use of such cellular testing is beneficial since it identifies those compounds which are able to enter mammalian cells and inhibit Rev function within the cells. In a modification of this technique, it would also be possible to express a test polypeptide in situ within the test cell. That is, the test cell would be transformed or transfected with a DNA construct expressing the polypeptide to be tested, either by itself or as a fusion gene product. Expression of mutant Rev polypeptide fused to the C-terminus of the HIV Tat protein have been shown to bind the RRE in the Experimental Section hereinafter.

The present invention further comprises methods for inhibiting Rev function and HIV-1 replication in cells, where the method includes administering to the cells any of the compounds described above and/or selected by the methods described above. The compounds may be added to cell culture in order to provide the desired inhibition. The compounds may also be administered to a patient in order to inhibit HIV-1 replication within the cells of the patient.

The present invention still further comprises pharmaceutical compositions incorporating an active molecule or compound according to the present invention and including a pharmaceutically-acceptable carrier. Such pharmaceutical compositions should contain a therapeutic or prophylactic amount of at least one compound as described above. The pharmaceutically acceptable carrier can be any compatible, non-toxic substance suitable to deliver the compound to an intended host. Sterile water, alcohols, fats, waxes, and inert solids may used as the carrier. Pharmaceutically acceptable adjuvents, buffering agents, dispersing agents, and the like, may also be incorporated into the pharmaceutical compositions. Preparation of pharmaceutical compositions incorporating active agents is well-described in the medical and scientific literature. See, for example, Remington's Pharmaceutical Sciences, Mack Publishing Company, Easton, Pa., 16th edition, 1982.

The pharmaceutical compositions just described are suitable for systemic administration to a host, including both parenteral and oral administration, particularly parenteral administration, i.e., subcutaneous, intramuscular, and intravenous. Thus, the present invention provides compositions for administration to a host, where the compositions comprise a pharmaceutically acceptable solution or suspension of the identified active compound in an acceptable carrier. The concentration of the active compound in the pharmaceutical carrier may vary widely, i.e., from less than about 0.1% by weight of the composition to about 20% by weight, or greater. Typical pharmaceutical compositions for intramuscular injection would be made up to contain, for example, 1 to 4 ml of sterile buffered water and 1 μg to 1 mg of the compound of the present invention.

The pharmaceutical compositions of the present invention can be administered for prophylactic and/or therapeutic treatment of HIV-1 infection. In therapeutic applications, the pharmaceutical compositions are administered to a host already suffering from HIV-1 infection. The pharmaceutical compositions will be administered in an amount sufficient to inhibit HIV-1 replication within diseased cells within the host. An amount adequate to accomplish this is defined as a "therapeutically effective dose." Such effective doses will depend on the extent of the disease, the size of the host, and the like, but will generally range from about 0.1 μg to 10 mg of the compound per kilogram of body weight of the host, with dosages of from 0.1 μg to 1 mg/kg being more commonly employed.

The following examples are offered by way of illustration, not by way of limitation.

EXPERIMENTAL

PROCEDURES

Peptide synthesis, purification, and analysis

Peptides I–V (FIG. 2) were synthesized on a Milligan/Biosearch model 9600 synthesizer as previously reported using PyBOP reagent (Novabiochem) in place of BOP in the standard BOP+HOBt coupling programs. Peptides containing alanins and proline mutations were prepared by multiple peptide synthesis using an Abimed 422 synthesizer and standard programming. Protecting groups used were: 2,2,5,6,7-pentamethyl chroman-6-sulfonyl (Pmc), Arg; trityl (Trt), Gln, Ash; t-butyl ester (OtBu), BlU; t-butyl (tBu), Thr; t-butyloxycarbonyl (tBOC), Trp. Syntheses with unprotected Trp resulted in extensive addition of pentaethylchromane-sulfonyl to the indole ring, even in the presence of thiol of silyl based scavengers. PAL-PEG-PS resin (Millipore) was used for the synthesis of peptides with C-terminal amides; peptides with unblocked C-terminal were synthesized using Arg(Pmc)-PAC-PEG-PS, prepared by coupling hydroxymethylphenoxyacetic acid to ethylenediamine-functionalized PEG-PS and then adding Pmos-Arg (Pmc)-OH.

Acetylation of the completed peptide resins was performed with 0.3M acetic anhydride +0.3M 1-hydroxybenzotriazole in DMF. Succinylation was performed with 0.3M succinic anhydride +0.3M 1-hydroxybenzotriazole +0.03M dimethylaminopyridine in DMF. Cleavage of multiply synthesized peptides was performed automatically with Reagent R using a Gilson autosampler system as described (Buettner, et al. Computer Directed Mass-Production of Peptides. In Peptides 1992: *Proceedings of the Twenty Second European Peptide Symposium*, A. Eberle and C. H. Schneider, eds. (Leiden:ESCOM). Other peptides were cleaved manually.

Amino acid composition was determined by hydrolysis in 6 M HCl at 156° C. for 90 min on a Water Pico-Tag workstation followed by analysis with a Hewlett Packard Aminoquant 1090M with PASCAL workstation and standard OPA/Fmoc chemistry. Peptides were purified on a $C_4$ reverse-phase HPLC column (Vydac) using an acetonitrile gradient of 0.2%/min in 0.1% trifluoroacetic acid. Peptide absorption spectra were recorded and concentrations of most peptides were determined by tryptophan absorbance at 278 nm ($\epsilon$=5600 $M^{-1}cm^{-1}$; Creighton, T. E. (1993), Proteins: *Structures and Molecular Properties*. New York: W. H. Freeman and Co.) The concentrations of non-tryptophan-containing peptides were determined by peptide absorbance at 229 nm using known peptide standards. Purity and concentrations were confirmed by native gel electrophoresis (20% polyacrylamide in 30 mMNa acetate, pH 4.5) in which peptides were visualized by Coomassie blue staining. Peptide molecular weights were confirmed by mass spectrometry on a Finnegan SSQ-700 spectrometer with electrospray ionization.

RNA synthesis and purification

Wild-type mutant IIB RNAs were transcribed in vitro by T7 RNA polymerase using synthetic oligonucleotide templates (Milligan et al. Synthesis of Small RNAs Using T7 RNA Polymerase. Methods Enzymol. 180:51–62.) All RNAs contained GC at the 5' end, which increases the efficiency of transcription, and CC at the 3' end to base pair with the G's. For randomly labeled RNA, $[\alpha^{-32}P]$ CTP (NEN, 3000 Ci/mmol) was included in the transcription reaction. RNAs were purified on 20% polyacrylamide/8 M urea gels, eluted from the gels in 0.5 M ammonium acetate, 1 mM EDTA, 0.1% SDS, and ethanol precipitated. Purified RNA was resuspended in sterile deionized water. The concentrations of radiolabeled RNAs were determined from the specific activity of $^{32}$P CTP incorporated into the transcripts. Unlabeled RNA was quantitated by spectrophotometry. RNAs were renatured by incubating in renaturation buffer (20 mM Tris-Cl, pH 7.5, 100 mM NaCl) for 2 min at 90° C. followed by slow cooling to room temperature.

RNA-binding gel shift assays

Gel shift assays were performed at 4° C. unless described otherwise. Peptide and RNA were incubated together for 15 min on ice in 10 µl binding reactions containing 10 mM HEPES-KOH, pH 7.5, 100 mM KCl, 1 mM MgCl$_2$, 0.5 mM EDTA, 1 mM dithithreitol, 50 µg/ml E. coli tRNA, and 10% glycerol. To determine relative binding affinities, 0.5 nM radiolabeled IIB RNA (or IIB mutant) was titrated with peptide. Peptide-RNA complexes were resolved in 10% polyacrylamide, 0.5x TBE gels that had been prerun for 1 hr and allowed to cool to 4° C. Gels were electrophoresed at 220 V for 3 hr at 4° C., dried, and autoradiographed.

Circular dichroism

CD spectra were measured using an Aviv model 62DS spectropolarimeter. Samples were prepared in 10 mM potassium phosphate buffer, pH 7.5 and 100 mM KF, and temperature was maintained at 4° C. unless described otherwise. Spectra were recorded from 320 nm to 190 nm using a 1 cm pathlength cuvette and the signal was averaged for 10 sec. Scans were repeated five times and averaged. Peptide concentrations were typically 5–20 µM and ellipticity was calculated per amino acid residue.

Construction of plasmids and CAT assays

The RRE IIB reporter plasmid was constructed by cloning synthetic oligonucleotide cassettes into the HIV LTR of pHIV-CAT as described (Tao et al. Electrostatic Interactions Modulate the RNA-Binding and Transactivation Specificities of the HIV and SIV Tat Proteins. Proc. Natl. Acad. Sci. USA 90, 1571–1575). Tat-Rev peptide hybrids were constructed by cloning Rev peptide-encoding cassettes into the tat gene of pSV2tat72 (Frankel, et al. (1988) "Cellular Uptake of the Tat Protein From Human Immunodeficiency Virus." Cell 55:1189–1193) after Tat amino acid 48. A Tat mutant truncated at the C-terminus of the Tat RNA-binding domain (amino acid 58) was also constructed. Mutations were confirmed by dideoxynucleotide sequencing. Reporter plasmids (50 ng) and Tat or Tat-Rev peptide fusion plasmids (50–200 ng) were transfected into HeLa cells and CAT activity was assayed after 48 hr as described (Calnan, et al. (1991a). Analysis of Arginine-Rich Peptides From the HIV Tat Protein Reveals Unusual Features of RNA-Protein Recognition. Genes Dev. 5:207–210). Total plasmid concentrations were adjusted to 1 µg total DNA with nonspecific pUC18 DNA.

RESULTS

Specific binding of a Rev peptide to RRE IIB RNA

Figure 1A:
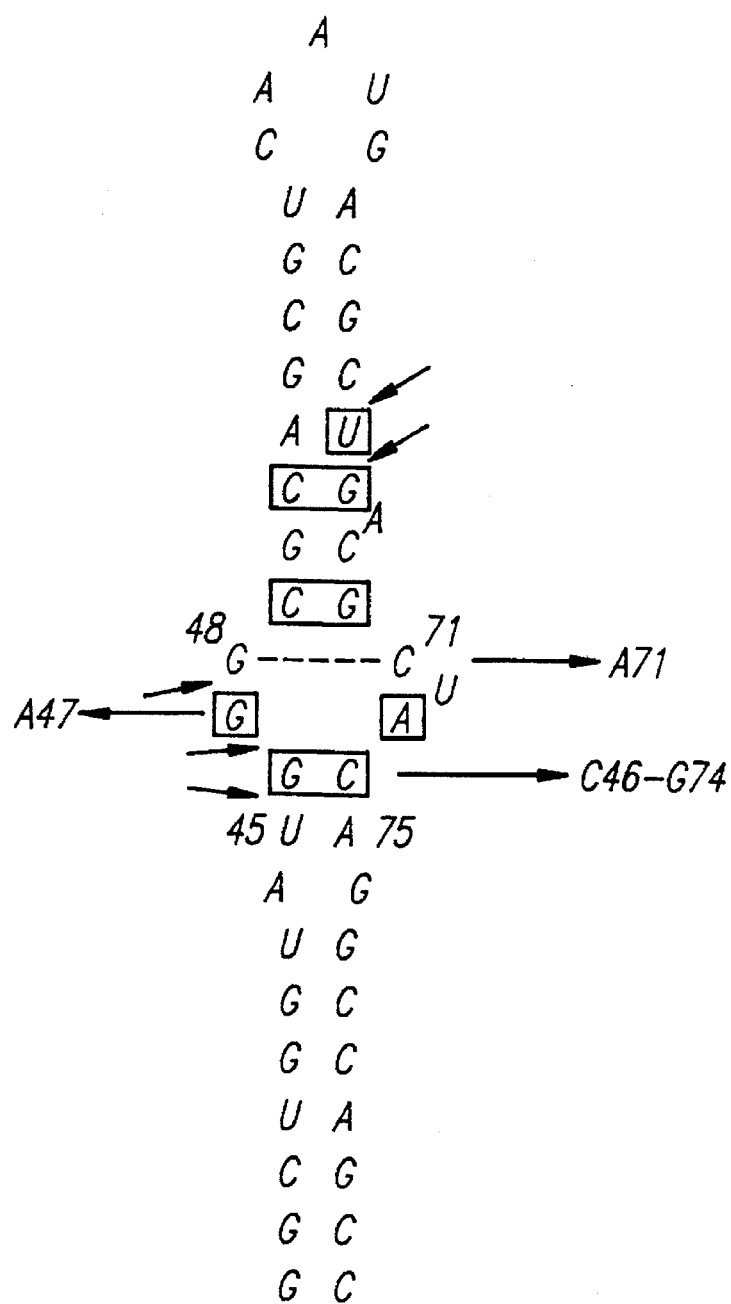
FIG. 1 (parts A–B) is a schematic illustration of the binding of $Rev_{34-50}$ (SEQ ID NO:1) to RRE IIB (SEQ ID NO:2), with important binding nucleotides being boxed.
FIG. 1B presents the results of gel shift binding assays between the Rev peptide and RRE IIB mutants.
Figure 1B:

A 17-amino acid peptide containing the arginine-rich region of Rev (amino acids 34–50; FIG. 1A) binds to the RRE and to the high-affinity IIB stem-loop (FIG. 1A) with similar specificity as intact Rev (Kjems, et al. (1992) Specific Binding of a Basic Peptide from HIV-1 Rev. EMBO J. 11:1119–1129). To further examine the binding specificity of Rev$_{34-50}$ and to identify RNAs that bind nonspecifically but contain only small changes in IIB structure, we measure peptide binding to two point mutants of IIB and to a single base pair substitution mutant known to reduce Rev-binding affinity (see FIG. 1A). Mutation of G71 (to A71) or G47 (to A47) in the asymmetric internal bulge, or mutation of the G46-C74 base pair (to C46-G74), reduced Rev$_{34-50}$ affinity by about 10-fold compared to wild-type IIB (FIG. 1B). These results are consistent with chemical modification and mutational studies using intact Rev (Bartel, et al. (1991) "HIV-1 Rev Regulation Involves Recognition of Non-Watson-Crick Base Pairs in Viral RNA." Cell 67:529–536; Kjems et al. (1991) "Structural Analysis of the Interaction Between the Human Immunodeficiency Virus Rev Protein and the Rev Response Element." Proc. Natl. Acad. Sci. USA 88:683–687; Tiley, et al. (1992b) "Identification of a High-Affinity RNA-Binding Site for the Human Immunodeficiency Virus Type 1 Protein." Proc. Natl. Acad. Sci. USA 89:758–762) and further indicate that the Rev peptide and protein bind to RNA in a similar manner.

Rev$_{34-50}$ forms an α-helix in solution

In contrast to the flexible sequence requirements of the Tat peptide for TAR binding (Calnan et al. supra.; Tao et al. supra.), the precise sequence of the Rev peptide is important for RRE IIB binding. Thus, the Rev peptide may adopt a particular structure and several amino acids, rather than a single arginine, may participate in sequence-specific RNA interactions.

To test whether the Rev peptide formed any structure in solution, we measured the circular dichroism (CD) spectrum of N-Rev$_{34-50}$—am, the peptide used in FIG. 1B and in a previous binding study (Kjems et al. (1992) supra.) This particular peptide has a free amino terminus and an amidated carboxyl terminus. Surprisingly, even though it is a short peptide with ten charged arginine residues, N-Rev$_{34-50}$—am contains approximately 4% α-helix at 4° C. (FIG. 2; peptide II; calculated from the CD minimum at 222 nm).

The helical conformation of short peptides can often be stabilized by modifying their termini such that favorable electrostatic interactions can occur with the helix macrodipole (Marqusee, et al. (1989). "Unusually Stable Helix Formation in Short Alanine-Based Peptides." Proc. Natl. Acad. Sci. USA 86:5286–5290); the additional arginine was added to maintain the C-terminal charged residue. The extent of helix formation is similar when four alanine are added to theN-terminus, and adding alanine to both ends increases helicity slightly to 57% (data not shown). For all peptides, helical content is independent of peptide concentration (1–40 µM; data not shown), suggesting that they are monomeric and do not aggregate. The double minima observed at 208 nm and 222 nm (see peptide V, FIG. 2) are characteristic of a high helical content; this degree of helix formation is unusual for such short peptides, even for peptides that are not so highly charged (Marqusee et al., supra.)

α-helix formation correlates with specific binding to IIB

Having established that the Rev$_{34-50}$ peptide can form a relatively stable α-helix when its ends are appropriately modified, we wished to assess the effect of helix formation on RNA-binding activity. Gel shift experiments were performed with IIB RNA and with the C46-G74 base pair mutant to compare specific and nonspecific binding of the give peptides shown in FIG. 2. Peptides were titrated with fixed amounts of wild-type or mutant IIB RNAs in the presence of competitor tRNA. When the peptide is in a random conformation (peptide I), it is essentially unable to discriminate between wild-type and mutant RNAs and binds with only slightly higher affinity to wild-type (FIG. 3A). As the helical content increases (peptides II–V), the affinity for wild-type IIB increases whereas the affinity for the mutant RNA is unchanged (FIG. 3B). The slight increase in non-specific affinity with peptide V is probably due to the additional arginine at its C-terminus. Similar binding results were obtained with the other mutant IIB RNAs described above, and peptide titrations in the absence of competitor indicated 1:1 stoichiometries for all complexes (data not shown). The second complex observed with the mutant RNA (see 60000 nM lanes; FIGS. 3A and 3B) probably represents two peptides bound nonspecifically, as seen within peptide-TAR complexes (Weeks et al. (1991) "RNA Recognition by Tat-Derived Peptides: Interaction in the Major Groove?" Cell 66:577–588).

Figure 3A:
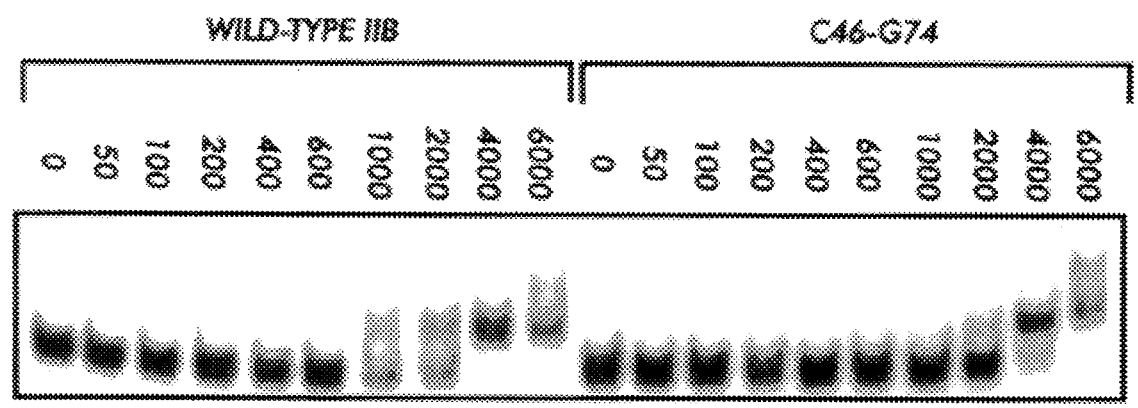
FIG. 3A presents the results of gel shift assays comparing the binding of wild-type and mutant RRE IIB with peptide I (FIG. 2).
Figure 3B:
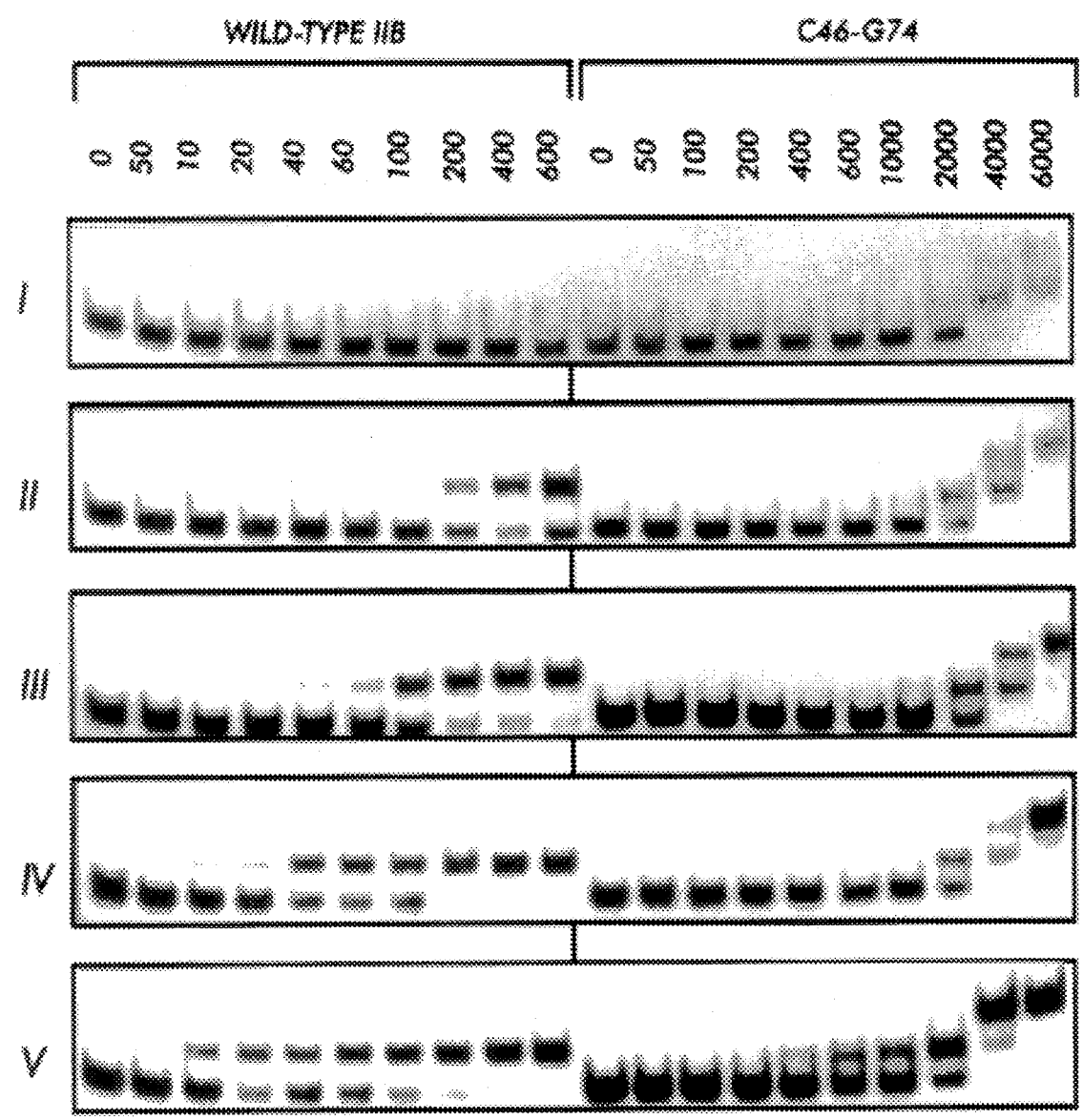
FIG. 3B presents the results of gel shift assays between wild-type and mutant RRE IIB with peptides I–V (FIG. 2).
Figure 3C:
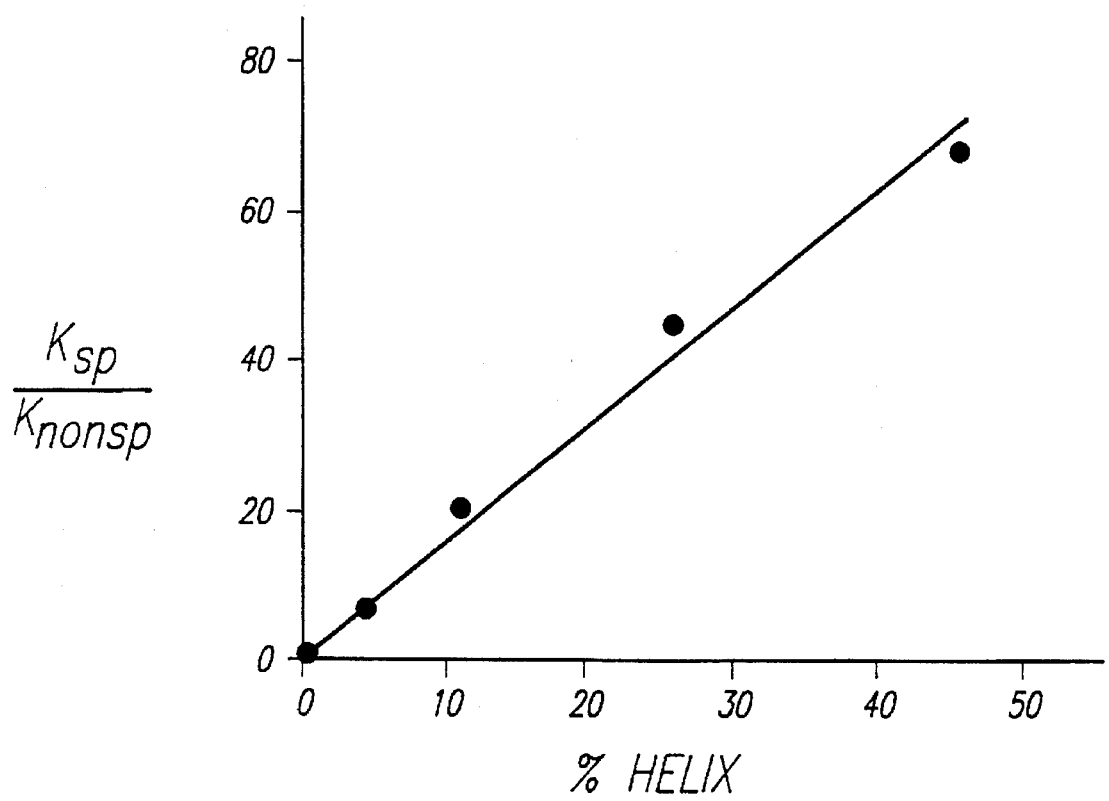
FIG. 3C is a graph illustrating the relationship between α-helical content of the Rev peptide and binding specificity.

A plot of α-helix content versus RNA-binding specificity (the ratio of specific to nonspecific RNA-binding association constants from FIGS. 3A and 3B) shows a linear relationship (FIG. 3C). Extrapolation to 100% helix corresponds to a specificity ratio of ≈150. Because helix formation is thermodynamically linked to specific RNA binding, one can estimate ΔG for the helix-coil transition to be ≈3 kcal/mol, assuming a two-state transition. It is not possible to directly measure the equilibrium constant of the specific α-helix-IIB RNA interaction by the gel shift assay (in the absence of competitor RNA) because the peptides are in a conformational equilibrium and apparent Kds would contain both specific and nonspecific contributions. However, because nonspecific $K_d$s can be measured directly using mutant "RNAs" in the absence of competitor, and because relative specific and nonspecific $K_d$s can be determined in the presence of competitor (unstructured peptides will bind preferentially to the excess unlabeled competitor (unstructured peptides will bind preferentially to the excess unlabeled competitor), we can estimate specific binding constants. For the most structured peptide, suc-Rev$_{34-50}$-AAAAR-am (SEQ ID NO:6, the measured nonspecific $K_d$s is 1.0±0.2 nM (data not shown) and the estimated specific $K_d$ (75-fold lower than the nonspecific $K_d$; Table I) is 0.013 nM.

TABLE I

α-Helix Content and RNA-Binding Affinities of Mutant Rev$_{34-50}$ Peptides

| Mutant | % Helix | $K_{sp}$ (nM) | $K_{nonsp}$ (nM) | Specificity | |
|---|---|---|---|---|---|
| 34 T → A | 28.6 | 700 | 1500 | 2.5 | ● |
| 35 R → A | 33.4 | 350 | 1500 | 4.3 | ● |
| 36 Q → A | 25.6 | 40 | 1600 | 40 | |
| 37 A (wild-type) | 27.9 | 40 | 2000 | 50 | |
| 38 R → A | 37.0 | 500 | 2000 | 4 | ● |
| 39 R → A | 29.8 | 500 | 2000 | 4 | ● |
| 40 N → A | 25.3 | 1600 | 5000 | 3.1 | ● |
| 41 R → A | 37.3 | 65 | 3000 | 46 | |
| 42 R → A | 34.0 | 35 | 2000 | 57 | |
| 43 R → A | 26.4 | 30 | 1500 | 50 | |
| 44 R → A | 26.5 | 900 | 2000 | 2.5 | ● |
| 45 W → A | 20.3 | 40 | 2000 | 50 | |
| 46 R → A | 30.6 | 300 | 2000 | 7 | ○ |
| 47 E → A | 19.6 | 50 | 2000 | 40 | |
| 48 R → A | 23.2 | 100 | 2000 | 20 | ○ |
| 49 Q → A | 28.2 | 40 | 3000 | 75 | |
| 50 R → A | 28.6 | 150 | 2000 | 13 | ○ |

Apparent $K_d$'s ($K_{sp}$ and $K_{nonsp}$), specificity, and % helix were determined as in FIG. 3. Closed circles (●) indicate substitutions that have a large effect on RNA-binding specificity and open circles (○) indicate those that have a relatively smaller effect.

Helix content was also varied by changing temperature or solvent conditions, with corresponding changes in RNA-binding specificity. Increasing temperature (from 4° C. to 25° C.) significantly unfolded the helix and reduced specific RNA-binding affinity, while addition of trifluoroethanol (TFE), a helix-stabilizing solvent, increased helix content and RNA-binding specificity (data not shown).

A proline mutant abolishes α-helix formation and specific RNA binding

Figure 4B:
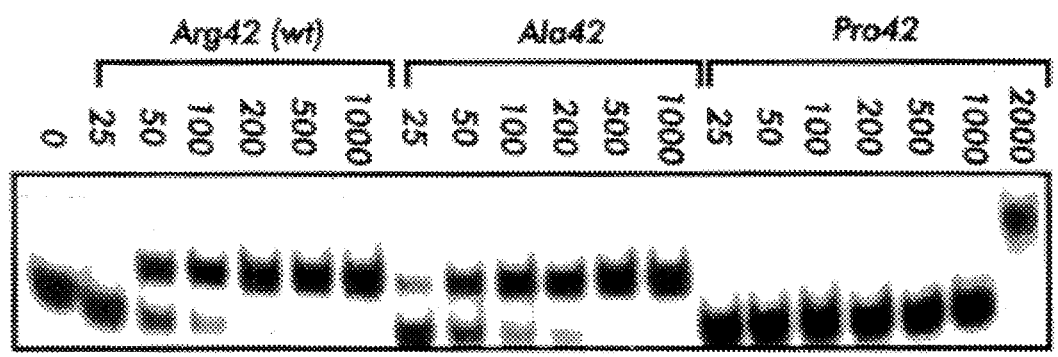
FIG. 4B presents the results of gel shift binding assays with the mutants of FIG. 4A.

To further test the importance of the α-helix for specific RNA binding, we asked whether introduction of a proline mutation, expected to disrupt the helix, would affect peptide binding to IIB. We first determined that Arg42, located in the middle of the peptide, was not involved in a direct contact with IIB (see below), and then synthesized suc-Rev$_{34-50}$—am (SEQ ID NO:5) derivatives having proline or alanine at this position (the wild-type peptide contains 28% α-helix). CD spectra indicate that the proline mutation entirely eliminates the α-helix whereas the alanine mutant shows similar helical content to the wild-type peptide (FIG. 4A). Gel shift assays with wild-type and mutant IIB RNAs show that α-helix content does indeed correlate with specific RNA binding; the proline mutant does not discriminate between wild-type and mutant RNAs whereas the alanine mutant binds as well as the wild-type peptide (FIG. 4B).

Specificity determinants within the peptide

To identify amino acids that might directly contact the RNA, a series of suc-Rev$_{34-50}$—am derivatives was synthesized with alanine substituted at each position, and binding affinities were measured using wild-type and mutant IIB RNAs. Six mutations were found to strongly decrease RNA-binding specificity—substitution of four arginines at positions 35, 38, 39, and 44, threonine at position 34, and asparagine at position 40 (Table I). In each case, the mutant peptide showed only marginal (2.5–4-fold) discrimination between wild-type and mutant IIB RNAs but, as for all the mutants, had a helical content similar to the wild-type peptide (Table I). Thus, these six mutations may remove direct RNA contact rather than destabilize the structure of the peptide, although subtle changes in peptide structure that are beyond detection by CD cannot be ruled out. Smaller decreases in RNA-binding specificity were observed with Arg46, Arg48, and Arg50 mutants (Table I), suggesting that these side chains may provide additional interactions.

In vivo evidence for helix formation

Figures 5A, 5B:
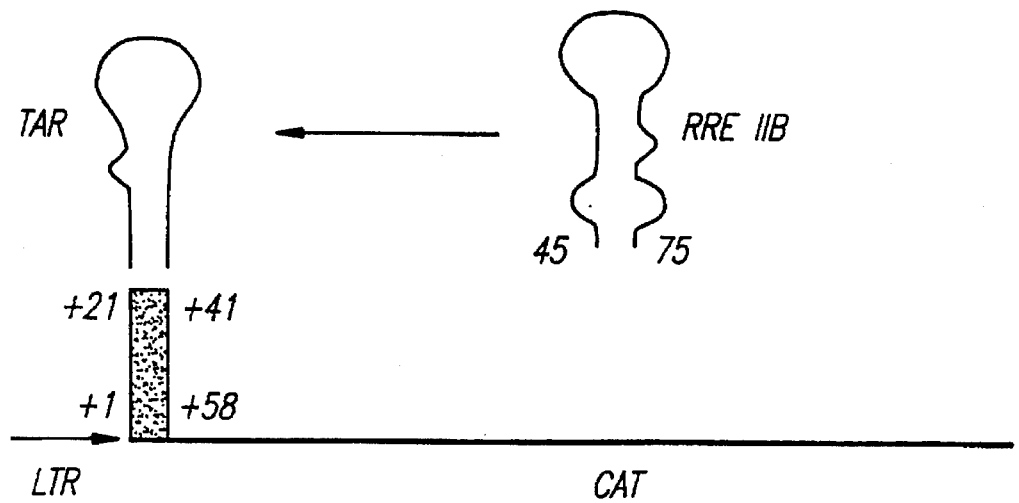
FIG. 5A is a schematic illustration of CAT assays with Tat-Rev peptide hybrids (TRQARRNRRRRWRERQR=SEQ ID NO:1; AAAATRQARRNRRRRWRERQR=SEQ ID NO:7; TRQARRNRRRRWRERQRAAAAR=SEQ ID NO:8; AAAATRQARRNRRRRWRERQRAAAAR=SEQ ID NO:9; RKKRRQRRRP=SEQ ID NO:10) and RRE IIB reporter described in detail in the Experimental section.
FIG. 5B illustrates the Tat-Rev peptide hybrids utilized in the CAT assays.

To address whether the α-helical structure is important for RNA-binding in vivo, we constructed an HIV-LTR-CAT reporter in which the TAR stem-loop was replaced by the RRE IIB stem-loop (FIG. 5A) and constructed Tat expression vectors in which Rev peptides were fused to the activation domain (residues 1–48) of Tat (FIG. 5B). With this system, Rev peptide binding to IIB could be monitored using Tat transactivation as a readout. Similar targeting of Tat has been reported using heterologous RNA-binding sites and Tat fusions with the MS2 coat protein or intact Rev protein.

When Rev$_{34-50}$ was fused to the C-terminus of Tat (fusion I; FIG. 5B), a low level of transactivation was observed through the IIB reporter (FIG. 5C), suggesting that the peptide with a free C-terminus does not bind well to IIB and may be largely unstructured. When four alanines were added to either the N- or C-terminus of Rev$_{34-50}$ (fusions II and III), stronger activation was observed, indicating increased RNA binding and correlating with in vitro stabilization of the α-helix. Addition of alanines at the C-terminus showed slightly higher transactivation than addition at the N-terminus, perhaps reflecting an unfavorable interaction of the terminal COO$^-$ group of the fusion protein with the Rev$_{34-50}$ helix macrodipole or reflecting addition of an extra arginine at the C-terminus. When alanines were added at both termini (fusion IV), even greater transactivation was observed, suggesting further stabilization of the α-helix.

Figure 5C:
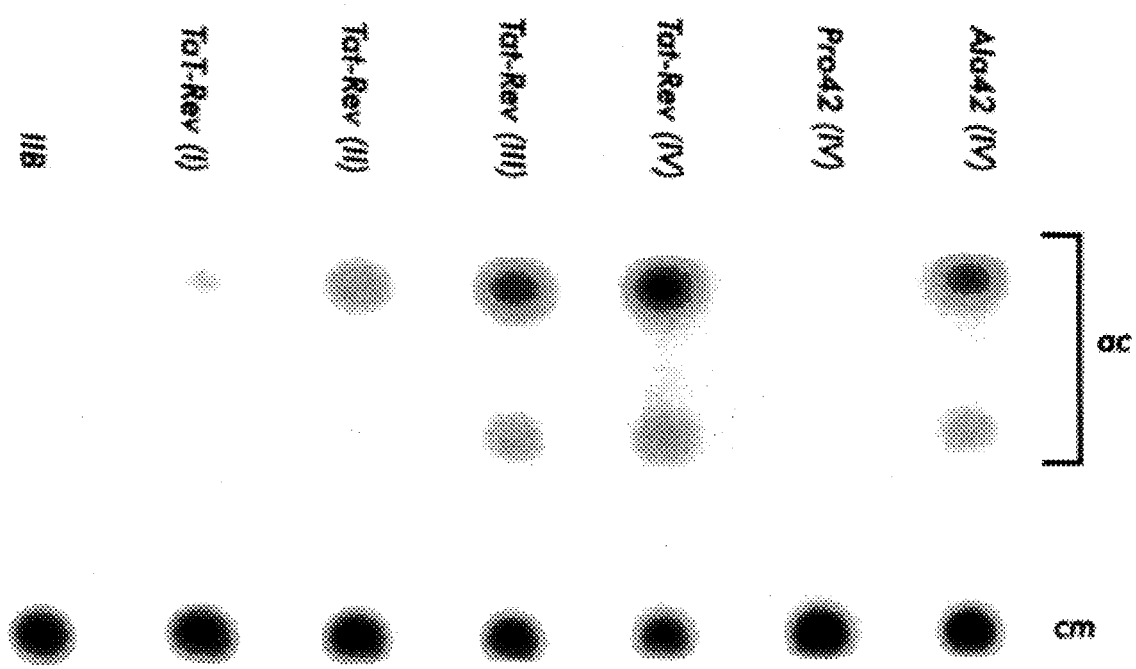
FIG. 5C presents the results of the CAT assays.

Mutations were introduced into the AAAA-Rev$_{34-50}$-AAAAR (SEQ ID NO:5) Tat fusion protein (fusion IV) to further test Rev$_{34-50}$ helix formation in vivo. In vitro experiments demonstrated that a proline mutation at position 42 eliminates helix formation and specific IIB binding whereas an alanine mutation has little effect (FIG. 4). In the corresponding fusion proteins, the proline mutant showed no transactivation through IIB while the alanine mutant was almost as active as wild-type (FIG. 5C). In contrast, substitution of Asn40 with alanine, which may remove a specific RNA contact, shows no activity (data not shown). Thus, it appears that Rev$_{34-50}$ must be in a α-helical conformation to bind IIB RNA in vivo.

FIGURE LEGENDS

FIG. 1A. Binding of Rev$_{34-50}$ to RRE IIB RNA and IIB Mutants and Sequences of Rev$_{34-50}$ and RRE IIB. The boxed nucleotides in IIB were shown to be important for Rev binding by mutagenesis, chemical interference, and in vitro RNA selection experiments (Bartel et al. (1991) "HIV-1 Rev Regulation Involves Recognition of Non-Watson-Crick Base Pairs in Viral RNA," Cell 67:529–536; Kjems et al. (1991) "Structural Analysis of the Interaction Between the Human Immunodeficiency Virus Rev Protein and the Rev Response Element" Proc. Natl. Acad. Sci. USA 88:683–687; Kjems et al. (1992) "Specific Binding of a Basic Peptide From HIV-1 Rev" EMBO J. 11:1119–1129; Tiley et al. (1992b) "Identification of a High-Affinity RNA-Binding Site for the Human Immunodeficiency Virus Type 1 Rev Protein" Proc. Natl. Acad. Sci. USA 89:758–762). Arrows indicate positions of phosphates whose modification interferes with binding (Kjems et al. (1992) supra). An important non-Watson-Crick base pair between G48 and G71, identified by in vitro RNA selection (Bartel et al., (1991) supra), is indicated by the dashed line. The three mutants used in this study (A47, A71, and C46-G74) were previously shown to decrease Rev binding affinity (Bartel et al. (1991), supra).

FIG. 1B. Peptide binding to IIB mutants. Binding reactions were carried out in the presence of tRNA at the peptide concentrations indicated, and free RNA and peptide-RNA complexes were resolved by the gel shift assay. Each pair of lanes corresponds to RNA alone and peptide-RNA binding reactions. Binding reactions with the mutants contained 10-fold more peptide than with wild-type IIB so that both the shifted and unshifted bands could be seen. The wild-type lanes on both sides of the gel are identical. The slower mobility of the A71 mutant in the absence of peptide may indicate that its unbound conformation is different than wild-type IIB. Note that all complexes formed with mutated RNAs displayed faster mobilities relative to the wild-type complex. This phenomenon has been seen with other mutant RNAs and with mutant Rev peptides, and has been interpreted as differences in RNA conformation between specific and nonspecific complexes (Kjems et al. (1992), supra).

Figure 2:
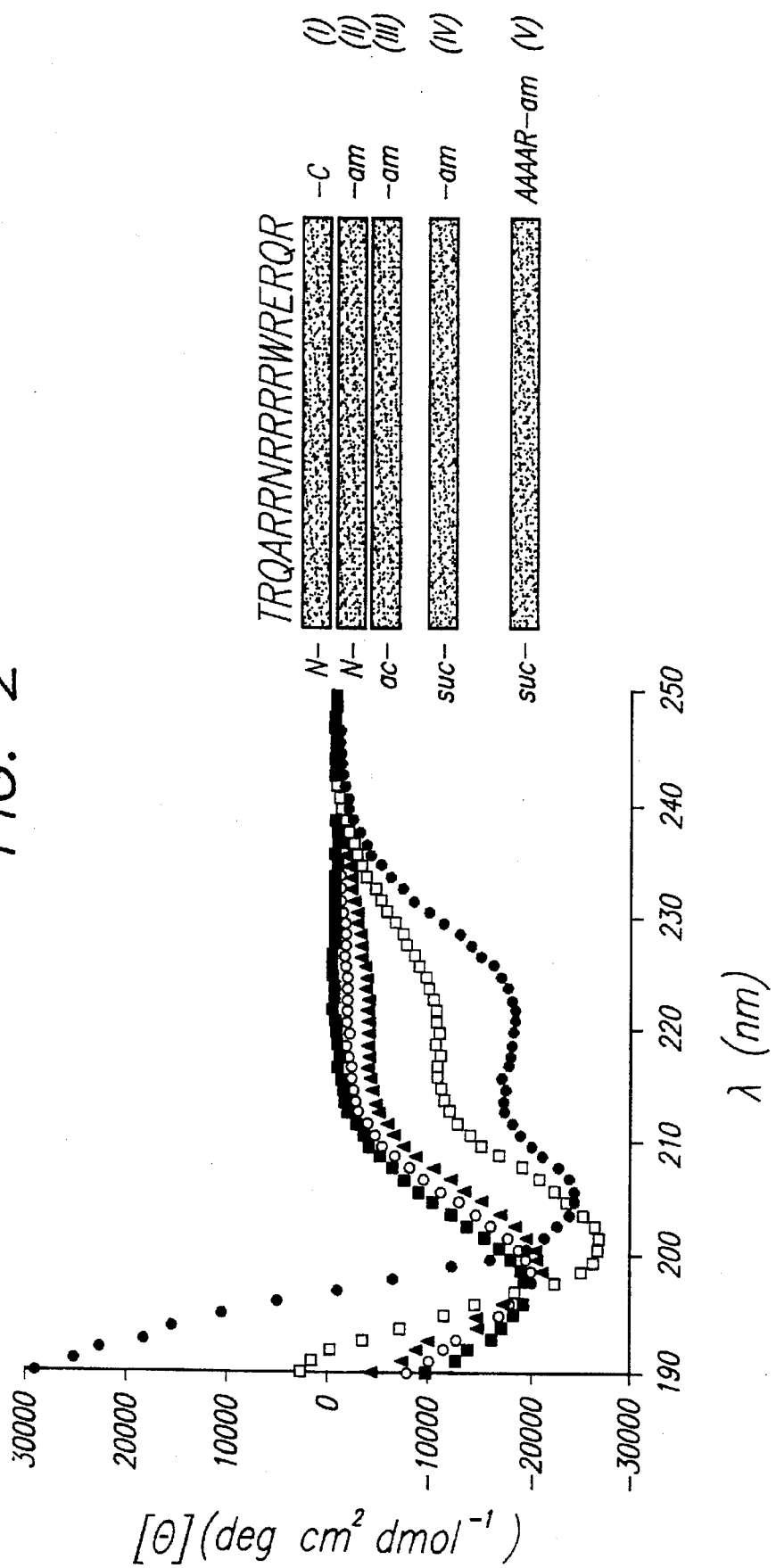
FIG. 2 presents circular dichroism spectra of peptides I–V (TRQARRNRRRRWRERQR=SEQ ID NO:1; peptide I=SEQ ID NO:1; peptide II=SEQ ID NO:3; peptide III=SEQ ID NO:4; peptide IV=SEQ ID NO:5; and peptide V=SEQ ID NO:6) having different levels of α-helical stability.

FIG. 2. α-Helix Formation Depends on the $Rev_{34-50}$ Peptide Termini with Circular dichroism spectra of the synthetic peptides shown. Peptide I (■) has unmodified N- and C-termini, peptide II (o) has a free N-terminus and an amidated C-terminus, peptide III (▲) has an acetylated N-terminus and an amidated C-terminus, peptide IV (□) has a succinylated N-terminus and an amidated C-terminus, and peptide V (●) has a succinylated N-terminus and an amidated C-terminus and contains four additional alanines and one additional arginine at its C-terminus. Double minima at 208 nm and 222 nm are indicative of α-helix formation, and helix content is proportional to the signal at 222 nm (see FIG. 3).

FIG. 3. Effect of α-Helix Content on RNA Binding. Titration of wild-type and mutant (C46-G74) IIB RNAs with peptide I at the concentrations indicated (nM). Binding reactions were carried out in the presence of tRNA and free RNA and peptide-RNA complexes were resolved by the gel shift assay. Peptide I, which is mostly unstructured, binds only slightly better to wild-type IIB than to the mutant RNA.

FIG. 3B. Titrations of wild-type and mutant IIB RNAs with peptides I-V at the concentrations indicated (nM). Binding reactions were described for FIG. 1A.

FIG. 3C. Relationship between helix content of the $Rev_{34-50}$ peptides and RNA-binding specificity. Apparent $K_d$s (the peptide concentration at which 50% of the RNA was shifted) were determined for wild-type (specific; $K_{sp}$) and mutant (nonspecific; $K_{nonsp}$) IIB RNAs from the date in FIGS. 3A and 3B. Specificity, the ratio of specific to nonspecific apparent association constants ($K_a$s) is plotted against the helix content for each peptide, determined from the CD ellipticity at 222 nm (Chen et al., (1974) "Determination of the Helix and Beta Form of Proteins in Aqueous Solution by Circular Dichroism" Biochemistry 13:3350–3359 ) Peptide I: helix=0.1%; $k_{sp}$=2000 nM; $K_{nonsp}$=3000 nM. Peptide II: helix=3.9%; $K_{sp}$=300 nM; $K_{nonsp}$=2000 nM. Peptide III: helix=10.9%; $K_{sp}$=100 nM; $K_{nonsp}$=2000 nM. Peptide IV: helix=27.9%; $K_{sp}$=40 nM; $K_{nonsp}$=2000 nM. Peptide V: helix=51.2%; $K_{sp}$=20 nM; $K_{nonsp}$1500 nM.

FIG. 4A. The α-Helix and Specific RNA Binding are Abolished by a Proline Mutation Circular dichroism spectra of Arg42→Pro, Arg42→Ala, and wild-type suc-$Rev_{34-50}$—am peptides. The spectrum of the proline mutant indicates a random coil while the spectrum of the alanine mutant indicates a helix content similar to the wild-type peptide.

FIG. 4B. RNA-binding gel shift assays with Arg42→Pro and Arg42→Ala mutants. Peptides were titrated at the concentrations indicated (nM) using wild-type IIB RNA. Binding reactions contained tRNA. Similar peptide titrations using the C46-G74 mutant RNA indicated that the nonspecific binding affinities were unchanged (data not shown).

FIG. 5A. CAT Assays with Tat-Rev Peptide Hybrids and the RRE IIB Report. An HIV LTR-CAT reporter plasmid was constructed in which the top part of the TAR stem-loop was replaced by the RRE IIB hairpin. TAR nucleotide numbers are relative to the transcription start site (+1) and IIB nucleotide numbers correspond to those in FIG. 1.

FIG. 5B. Plasmids expressing Tat-Rev peptide hybrids were constructed encoding the sequences shown. The Rev peptides were fused to the activation domain of Tat (amino acids 1–48), which is required for Tat transactivation. Also shown is a control Tat protein truncated at the C-terminus of the Tat RNA-binding domain (amino acid 58).

FIG. 5C. CAT assays of Tat-Rev peptide hybrids. Fusion proteins correspond to those in FIG. 5B. The Arg42→Pro and Arg42→Ala mutants were constructed within fusion protein IV. Acetylated (ac) and unacetylated (cm) [$^{14}$C] chloramphenicol are indicated. Tat truncated at the C-terminus of its own RNA-binding domain [see (B)] does not activate through the IIB reporter but strongly activates through TAR (data not shown).

FIG. 6A. Helical projection of $Rev_{34-50}$ showing amino acids whose mutation strongly (shaded circles) or weakly (open circles) decreases RNA-binding specificity.

FIG. 6B. Schematic drawings of the $Rev_{34-50}$ peptide-RNA complex. Four arginines, one threonine, and one aspargine (black side chains) from the Rev α-helix may recognize two bulge regions in HB RNA.

Although the foregoing invention has been described in detail for purposes of clarity of understanding, it will be obvious that certain modifications may be practiced within the scope of the appended claims.

5,654,398

---

What is claimed is:

1. A polypeptide having 30 or fewer amino acids with a stabilized electronic configuration and molecular conformation which binds to the IIB site of Rev-responsive element of HIV-1 with an affinity greater than that of the wild-type REV protein, wherein the α-helical conformation of said polypeptide is more stable than that of $Rev_{34-50}$.

2. A polypeptide having 30 or fewer amino acids and including at least six contiguous amino acids to provide a stabilized electronic configuration and α-helical conformation for binding to the IIB site of the Rev-responsive element of HIV-1 with an affinity greater than that of wild-type Rev protein, wherein said six contiguous amino acids are selected from the following sequence:

$T-A_1-X_1-X_2-A_2-A_3-A_s-X_3-X_4-X_5-A_4$ (SEQ ID NO:12)

wherein $X_{1-5}$ are L-amino acids and may be the same or different;

$A_{1-4}$ are arginine;

T is selected from the group consisting of threonine, serine, homothreonine, and dehydrothreonine; and $A_s$ is selected from the group consisting of asparagine and glutamine.

3. The polypeptide of claim 2 where X is selected from the group consisting of alanine and lysine.

4. The polypeptide of claim 2, including at least eight contiguous amino acids from SEQ ID NO:12.

5. The polypeptide of claim 2, including at least the eleven amino acids of SEQ ID NO:12.

6. The polypeptide of any one of claims 1, 2, 3, 4 and 5, further comprising stabilizing groups bound to the amino terminus, carboxy terminus, or both.

\* \* \* \* \*

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
        ( A ) LENGTH: 17 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO:1:

```
Thr  Arg  Gln  Ala  Arg  Arg  Asn  Arg  Arg  Arg  Trp  Arg  Glu  Arg  Gln
1                   5                        10                       15
Arg
```

( 2 ) INFORMATION FOR SEQ ID NO:2:

( i ) SEQUENCE CHARACTERISTICS:
        ( A ) LENGTH: 47 base pairs
        ( B ) TYPE: nucleic acid
        ( C ) STRANDEDNESS: both
        ( D ) TOPOLOGY: linear ( i i ) MOLECULE TYPE: RNA (genomic)

( x i ) SEQUENCE DESCRIPTION: SEQ ID NO:2:

```
GGCUGGUAUG  GGCGCAGCGU  CAAUGACGCU  GACGGUACAG  GCCAGCC                    47
```

( 2 ) INFORMATION FOR SEQ ID NO:3:

( i ) SEQUENCE CHARACTERISTICS:
        ( A ) LENGTH: 17 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( A ) NAME/KEY: Modified-site
        ( B ) LOCATION: 17
        ( D ) OTHER INFORMATION: /product="OTHER"
        / note= "Xaa = argininamide"

( x i ) SEQUENCE DESCRIPTION: SEQ ID NO:3:

```
Thr  Arg  Gln  Ala  Arg  Arg  Asn  Arg  Arg  Arg  Trp  Arg  Glu  Arg  Gln
1                   5                        10                       15
Xaa
```

( 2 ) INFORMATION FOR SEQ ID NO:4:

( i ) SEQUENCE CHARACTERISTICS:
        ( A ) LENGTH: 17 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /product="OTHER"
        / note= "Xaa = N-acetyl-threonine"

( i x ) FEATURE:
        ( A ) NAME/KEY: Modified-site
        ( B ) LOCATION: 17
        ( D ) OTHER INFORMATION: /product="OTHER"
                / note= "Xaa = argininamide"

( x i ) SEQUENCE DESCRIPTION: SEQ ID NO:4:

Xaa  Arg  Gln  Ala  Arg  Arg  Asn  Arg  Arg  Arg  Arg  Trp  Arg  Glu  Arg  Gln
1                   5                        10                       15

Xaa ( 2 ) INFORMATION FOR SEQ ID NO:5:

( i ) SEQUENCE CHARACTERISTICS:
        ( A ) LENGTH: 17 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /product="OTHER"
                / note= "Xaa = N-succinyl-threonine"

( i x ) FEATURE:
        ( A ) NAME/KEY: Modified-site
        ( B ) LOCATION: 17
        ( D ) OTHER INFORMATION: /product="OTHER"
                / note= "Xaa = argininamide"

( x i ) SEQUENCE DESCRIPTION: SEQ ID NO:5:

Xaa  Arg  Gln  Ala  Arg  Arg  Asn  Arg  Arg  Arg  Trp  Arg  Glu  Arg  Gln
1                   5                        10                   15

Xaa ( 2 ) INFORMATION FOR SEQ ID NO:6:

( i ) SEQUENCE CHARACTERISTICS:
        ( A ) LENGTH: 22 amino acids
        ( B ) TYPE: amino acid
        ( C ) STRANDEDNESS:
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /product="OTHER"
                / note= "Xaa = N-succinyl-threonine"

( i x ) FEATURE:
        ( A ) NAME/KEY: Modified-site
        ( B ) LOCATION: 22
        ( D ) OTHER INFORMATION: /product="OTHER"
                / note= "Xaa = argininamide"

( x i ) SEQUENCE DESCRIPTION: SEQ ID NO:6:

Xaa  Arg  Gln  Ala  Arg  Arg  Asn  Arg  Arg  Arg  Trp  Arg  Glu  Arg  Gln
1                   5                        10                   15

Arg  Ala  Ala  Ala  Ala  Xaa
                20

( 2 ) INFORMATION FOR SEQ ID NO:7:

( i ) SEQUENCE CHARACTERISTICS:
        ( A ) LENGTH: 21 amino acids (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:7:

Ala  Ala  Ala  Ala  Thr  Arg  Gln  Ala  Arg  Arg  Asn  Arg  Arg  Arg  Arg  Trp
    1                   5                        10                           15

Arg  Glu  Arg  Gln  Arg
                     20

(2) INFORMATION FOR SEQ ID NO:8:

(i) SEQUENCE CHARACTERISTICS:
        (A) LENGTH: 22 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:8:

Thr  Arg  Gln  Ala  Arg  Arg  Asn  Arg  Arg  Arg  Trp  Arg  Glu  Arg  Gln
    1                   5                        10                       15

Arg  Ala  Ala  Ala  Ala  Arg
                     20

(2) INFORMATION FOR SEQ ID NO:9:

(i) SEQUENCE CHARACTERISTICS:
        (A) LENGTH: 26 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:9:

Ala  Ala  Ala  Ala  Thr  Arg  Gln  Ala  Arg  Arg  Asn  Arg  Arg  Arg  Arg  Trp
    1                   5                        10                           15

Arg  Glu  Arg  Gln  Arg  Ala  Ala  Ala  Ala  Arg
                     20                       25

(2) INFORMATION FOR SEQ ID NO:10:

(i) SEQUENCE CHARACTERISTICS:
        (A) LENGTH: 10 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:10:

Arg  Lys  Lys  Arg  Arg  Gln  Arg  Arg  Arg  Pro
    1                   5                        10

(2) INFORMATION FOR SEQ ID NO:11:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (ix) FEATURE:

(A) NAME/KEY: Modified-site
(B) LOCATION: 1
(D) OTHER INFORMATION: /product="OTHER"
/note= "Xaa = preferably threonine, also
may be serine or mimetic threonine
derivatives, such as homothreonine,
dehydrothreonine, and the like"

(ix) FEATURE:
(A) NAME/KEY: Modified-site
(B) LOCATION: 2
(D) OTHER INFORMATION: /product="OTHER"
/note= "Xaa = preferably arginine, also
may be mimetic derivatives or arginine,
such as homoarginine, citrulline,
guanidophenylalanine, or other N-guanido
methylated forms"

(ix) FEATURE:
(A) NAME/KEY: Modified-site
(B) LOCATION: 3
(D) OTHER INFORMATION: /product="OTHER"
/note= "Xaa = preferably lysine or
alanine, also may be any natural or
unnatural L- amino acid"

(ix) FEATURE:
(A) NAME/KEY: Modified-site
(B) LOCATION: 4
(D) OTHER INFORMATION: /product="OTHER"
/note= "Xaa = preferably lysine or
alanine, also may be any natural or
unnatural L- amino acid"

(ix) FEATURE:
(A) NAME/KEY: Modified-site
(B) LOCATION: 5
(D) OTHER INFORMATION: /product="OTHER"
/note= "Xaa = preferably arginine, also
may be mimetic derivatives of arginine,
such as homoarginine, citrulline,
guanidophenylalanine, or other N-guanido
methylated forms"

(ix) FEATURE:
(A) NAME/KEY: Modified-site
(B) LOCATION: 6
(D) OTHER INFORMATION: /product="OTHER"
/note= "Xaa = preferably arginine, also
may be mimetic derivatives of arginine,
such as homoarginine, citrulline,
guanidophenylalanine, or other N-guanido
methylated forms"

(ix) FEATURE:
(A) NAME/KEY: Modified-site
(B) LOCATION: 7
(D) OTHER INFORMATION: /product="OTHER"
/note= "Xaa = preferably asparagine,
also may be serine or mimetic threonine
derivatives, such as homothreonine,
dehydrothreonine, or the like"

(ix) FEATURE:
(A) NAME/KEY: Modified-site
(B) LOCATION: 8
(D) OTHER INFORMATION: /product="OTHER"
/note= "Xaa = preferably lysine or
alanine, also may be any natural or
unnatural L- amino acid"

(ix) FEATURE:
(A) NAME/KEY: Modified-site
(B) LOCATION: 9
(D) OTHER INFORMATION: /product="OTHER"
/note= "Xaa = preferably lysine or
alanine, also may be any natural or
unnatural L- amino acid"

(ix) FEATURE:

(A) NAME/KEY: Modified-site
(B) LOCATION: 10
(D) OTHER INFORMATION: /product="OTHER"
/ note= "Xaa = preferably lysine or
alanine, also may be any natural or
unnatural L- amino acid"

(ix) FEATURE:
(A) NAME/KEY: Modified-site
(B) LOCATION: 11
(D) OTHER INFORMATION: /product="OTHER"
/ note= "Xaa = preferably arginine, also
may be mimetic derivatives of arginine,
such as homoarginine, citrulline,
guanidophenylalanine, or other N-guanido
methylated forms"

(xi) SEQUENCE DESCRIPTION: SEQ ID NO:11:

Xaa Xaa Xaa Xaa Xaa Xaa Xaa Xaa Xaa Xaa Xaa
1               5                   10

(2) INFORMATION FOR SEQ ID NO:12:

(i) SEQUENCE CHARACTERISTICS:
(A) LENGTH: 11 amino acids
(B) TYPE: amino acid
(C) STRANDEDNESS:
(D) TOPOLOGY: linear (ii) MOLECULE TYPE: peptide (ix) FEATURE:
(A) NAME/KEY: Modified-site
(B) LOCATION: 1
(D) OTHER INFORMATION: /product="OTHER"
/ note= "Xaa = threonine, serine,
homothreonine, or dehydrothreonine"

(ix) FEATURE:
(A) NAME/KEY: Modified-site
(B) LOCATION: 2
(D) OTHER INFORMATION: /product="OTHER"
/ note= "Xaa = arginine, homoarginine,
citrulline, guanidophenylalanine, or
other N- guanido methylated derivatives"

(ix) FEATURE:
(A) NAME/KEY: Modified-site
(B) LOCATION: 3
(D) OTHER INFORMATION: /product="OTHER"
/ note= "Xaa = any L-amino acid"

(ix) FEATURE:
(A) NAME/KEY: Modified-site
(B) LOCATION: 4
(D) OTHER INFORMATION: /product="OTHER"
/ note= "Xaa = any L-amino acid"

(ix) FEATURE:
(A) NAME/KEY: Modified-site
(B) LOCATION: 5
(D) OTHER INFORMATION: /product="OTHER"
/ note= "Xaa = arginine, homoarginine,
citrulline, guanidophenylalanine, or
other N- guanido methylated derivatives"

(ix) FEATURE:
(A) NAME/KEY: Modified-site
(B) LOCATION: 6
(D) OTHER INFORMATION: /product="OTHER"
/ note= "Xaa = arginine, homoarginine,
citrulline, guanidophenylalanine, or
other N- guanido methylated derivatives"

(ix) FEATURE:
(A) NAME/KEY: Modified-site
(B) LOCATION: 7
(D) OTHER INFORMATION: /product="OTHER"

/ note= "Xaa = asparagine, glutamine, or
citrulline"

( i x ) FEATURE:
 ( A ) NAME/KEY: Modified-site
 ( B ) LOCATION: 8
 ( D ) OTHER INFORMATION: /product="OTHER"
  / note= "Xaa = any L-amino acid"

( i x ) FEATURE:
 ( A ) NAME/KEY: Modified-site
 ( B ) LOCATION: 9
 ( D ) OTHER INFORMATION: /product="OTHER"
  / note= "Xaa = any L-amino acid"

( i x ) FEATURE:
 ( A ) NAME/KEY: Modified-site
 ( B ) LOCATION: 10
 ( D ) OTHER INFORMATION: /product="OTHER"
  / note= "Xaa = any L-amino acid"

( i x ) FEATURE:
 ( A ) NAME/KEY: Modified-site
 ( B ) LOCATION: 11
 ( D ) OTHER INFORMATION: /product="OTHER"
  / note= "Xaa = arginine, homoarginine,
  citrulline, guanidophenylalanine, or
  other N- guanido methylated derivatives"

( x i ) SEQUENCE DESCRIPTION: SEQ ID NO:12:

Xaa Xaa Xaa Xaa Xaa Xaa Xaa Xaa Xaa Xaa Xaa
1     5       10